US012784894B2

(12) United States Patent
Kim et al.

(10) Patent No.: US 12,784,894 B2
(45) **Date of Patent: *Nov. 3, 2026**

(54) METHOD AND SYSTEM FOR DETECTING PNEUMOTHORAX

(71) Applicants: Lunit Inc., Seoul (KR); SEOUL NATIONAL UNIVERSITY HOSPITAL, Seoul (KR)

(72) Inventors: Min Chul Kim, Seoul (KR); Chang Min Park, Seoul (KR); Eui Jin Hwang, Seoul (KR)

(73) Assignees: LUNIT INC., Seoul (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 184 days.

This patent is subject to a terminal disclaimer.

(21) Appl. No.: 18/650,347

(22) Filed: Apr. 30, 2024

(65) Prior Publication Data

US 2024/0282434 A1 Aug. 22, 2024

Related U.S. Application Data

(63) Continuation of application No. 18/086,977, filed on Dec. 22, 2022, now Pat. No. 11,996,184, which is a (Continued)

(30) Foreign Application Priority Data

Sep. 3, 2019 (KR) ........................ 10-2019-0109151

(51) Int. Cl.
*G16H 30/40* (2018.01)
*A61B 6/00* (2024.01)
(Continued)

(52) U.S. Cl.
CPC ........... *G16H 30/40* (2018.01); *A61B 6/5217* (2013.01); *A61B 34/10* (2016.02); *A61M 1/04* (2013.01);
(Continued)

(58) Field of Classification Search
CPC ......... A61B 6/461; A61B 6/527; A61B 34/10; A61B 2034/107; A61M 1/04;
(Continued)

(56) References Cited

U.S. PATENT DOCUMENTS

| | | | | |
|---|---|---|---|---|
| 2012/0263366 A1* | 10/2012 | Huo | G06T 5/92 | 382/132 |
| 2013/0197370 A1* | 8/2013 | Burlina | G06T 7/0016 | 600/476 |
| 2018/0047158 A1* | 2/2018 | Geva | G16H 50/30 | |

* cited by examiner

*Primary Examiner* — Katrina R Fujita
(74) *Attorney, Agent, or Firm* — LEX IP MEISTER, PLLC

(57) ABSTRACT

Some embodiments of the present disclosure provide a pneumothorax detection method performed by a computing device. The method may comprise obtaining predicted pneumothorax information, predicted tube information, and a predicted spinal baseline with respect to an input image from a trained pneumothorax prediction model; determining at least one pneumothorax representative position for the predicted pneumothorax information and at least one tube representative position for the predicted tube information, in a prediction image in which the predicted pneumothorax information and the predicted tube information are displayed; dividing the prediction image into a first region and a second region by the predicted spinal baseline; and determining a region in which the at least one pneumothorax representative position and the at least one tube representative position exist among the first region and the second region.

18 Claims, 8 Drawing Sheets

Related U.S. Application Data continuation of application No. 16/680,783, filed on Nov. 12, 2019, now Pat. No. 11,564,650.

(51) Int. Cl.

| | |
|---|---|
| ***A61B 6/46*** | (2024.01) |
| ***A61B 34/10*** | (2016.01) |
| ***A61M 1/04*** | (2006.01) |
| ***G06F 18/2431*** | (2023.01) |
| ***G06N 20/00*** | (2019.01) |
| ***G06T 7/00*** | (2017.01) |
| ***G06T 7/11*** | (2017.01) |
| ***G06T 7/70*** | (2017.01) |
| ***G06V 10/25*** | (2022.01) |
| ***G06V 10/764*** | (2022.01) |
| ***G06V 10/82*** | (2022.01) |
| ***G16H 50/20*** | (2018.01) |

(52) U.S. Cl.

CPC ......... *G06F 18/2431* (2023.01); *G06N 20/00* (2019.01); *G06T 7/0012* (2013.01); *G06T 7/11* (2017.01); *G06T 7/70* (2017.01); *G06V 10/25* (2022.01); *G06V 10/764* (2022.01); *G06V 10/82* (2022.01); *G16H 50/20* (2018.01); *A61B 6/461* (2013.01); *A61B 2034/107* (2016.02); *G06T 2207/20081* (2013.01); *G06T 2207/30012* (2013.01); *G06T 2207/30061* (2013.01); *G06V 2201/03* (2022.01)

(58) Field of Classification Search

CPC .... G16H 30/40; G16H 50/20; G06F 18/2431; G06N 20/00; G06T 7/0012; G06T 7/11; G06T 7/70; G06T 2207/20081; G06T 2207/30012; G06T 2207/30061; G06V 10/25; G06V 10/764; G06V 10/82; G06V 2201/03

See application file for complete search history.

METHOD AND SYSTEM FOR DETECTING PNEUMOTHORAX

CROSS-REFERENCE TO RELATED APPLICATION

This application is a Continuation Application of U.S. patent application Ser. No. 18/086,977 filed on Dec. 22, 2022, which is a Continuation Application of U.S. patent application Ser. No. 16/680,783 filed on Nov. 12, 2019, which claims priority to and the benefit of Korean Patent Application No. 10-2019-0109151 filed in the Korean Intellectual Property Office on Sep. 3, 2019, the entire contents of which are incorporated herein by reference.

BACKGROUND

(a) Field

The present disclosure relates to an artificial intelligence-based medical image analysis.

(b) Description of the Related Art

Pneumothorax is a disease in which the lungs are pressed to be unable to normally breathe when air is filled in a pleural cavity surrounding the lungs, causing symptoms of shortness of breath and chest pain. A cause of pneumothorax has not been revealed so far. There are no fundamental preventive measures therefor, and it can occur by various causes in younger age groups without lung disease.

Medical staff can diagnose pneumothorax through an X-ray image. When the pneumothorax is large or causes severe symptoms, a thin tube can be inserted into the chest to discharge the excess air. By quickly treating the pneumothorax, which is an emergency disease, a patient's breathing difficulties and chest pains can be alleviated and additional damage can be reduced.

Recently, an artificial intelligence technology has been applied to a medical image interpreting/reading/analysis field, thereby increasing accuracy and speed of image interpreting. Particularly, an artificial intelligence analysis has been developed that uses X-ray image analysis to mark sites with abnormal findings such as pulmonary nodules and to suggest their possibility as an index. Therefore, the pneumothorax may also be found to some extent through artificial intelligence image analysis.

However, the pneumothorax may be found in both lungs of a patient or in only one lung. Particularly, it is necessary to predict location (left lung side or right lung side) of the found pneumothorax along with the presence or absence of the pneumothorax, because emergency tube insertion is needed into the lung where the pneumothorax is founded. However, conventional image analysis systems that predict abnormal sites in a whole image have limitations in accurately predicting whether the found pneumothorax is located in left or right lung of a patient. Therefore, there is a need for an artificial intelligence image analysis method optimized for the pneumothorax.

The above information disclosed in this Background section is only for enhancement of understanding of the background of the invention, and therefore it may contain information that does not form the prior art that is already known in this country to a person of ordinary skill in the art.

SUMMARY

The present disclosure may provide a pneumothorax detection method and system that generate a pneumothorax prediction model that predicts pneumothorax from an image and determines a region where the pneumothorax is located among left and right regions of a patient, and uses a trained pneumothorax prediction model.

The present disclosure may provide an emergency pneumothorax detection method and system that generates a pneumothorax prediction model that simultaneously determines whether pneumothorax is present or not and where the pneumothorax is located, and whether a treated tube is present or not and where the tube is located, and uses a learned pneumothorax prediction model.

The present disclosure may provide a method and system that generates a spinal baseline being a reference for determining left and right regions of a patient in an image, and generating an image with left and right regions labeled based on the spinal baseline, as training data.

Some embodiments of the present disclosure provide a pneumothorax detection method performed by a computing device by at least one processor. The method may comprise obtaining predicted pneumothorax information, predicted tube information, and a predicted spinal baseline with respect to an input image from a trained pneumothorax prediction model; determining at least one pneumothorax representative position for the predicted pneumothorax information and at least one tube representative position for the predicted tube information in a prediction image in which the predicted pneumothorax information and the predicted tube information are displayed; dividing the prediction image into a first region and a second region by the predicted spinal baseline; and determining a region in which the at least one pneumothorax representative position and the at least one tube representative position exist among the first region and the second region.

The pneumothorax detection method may further include classifying the input image as an emergency pneumothorax when the tube representative position does not exist in the first region in which the at least one pneumothorax representative position exists.

The pneumothorax detection method may further include outputting information on the first region in which a tube insertion treatment is required, together with an alarm indicating the emergency pneumothorax.

The pneumothorax detection method may further include classifying the input image as a general pneumothorax when the tube representative position exists in the first region in which the at least one pneumothorax representative position exists.

The pneumothorax representative position and the tube representative position may be respectively determined, in the prediction image in which the predicted pneumothorax information or the predicted tube information is displayed as a predicted value, as at least one of a position at which the predicted value is a maximum value, a position of the maximum value in a region where the predicted value is greater than or equal to a threshold, and a position of a central value in the region in which the predicted value is greater than or equal to the threshold.

The pneumothorax detection method may further comprise training the pneumothorax prediction model for at least one task based on training images in which the first region and the second region separated by the spinal baseline are tagged with left and right determination labels. The at least one task may comprise a task of predicting pneumothorax information in the training images, a task of predicting a tube in the training images, and a task of predicting the spinal baseline in the training images.

Some embodiments of the present disclosure provide a pneumothorax detection method performed by a computing device. The pneumothorax detection method may comprise obtaining predicted pneumothorax information for an input image and a predicted spinal baseline for the input image, from a pneumothorax prediction model trained to predict pneumothorax by using training images tagged with left and right determination labels; and determining a pneumothorax presence region among left and right regions of a patient by using the predicted pneumothorax information and the predicted spinal baseline. The left and right determination labels may include region information separated based on the spinal baseline of each training image.

The pneumothorax detection method may further comprise, when the pneumothorax prediction model is trained to further predict a tube in the training images, obtaining predicted tube information for the input image from the pneumothorax prediction model; determining a tube presence region among the left and right regions of the patient by using the predicted tube information and the predicted spinal baseline; and classifying the input image as an emergency pneumothorax when the pneumothorax presence region is the first region, and the tube presence region is the second region or the tube presence region does not exist among the left and right regions of the patient.

Some embodiments of the present disclosure provide a pneumothorax detection method performed by a computing device operated by at least one processor The pneumothorax detection method may comprised receiving training images; separating spinal regions from each training image and generating a spinal baseline representative of the spinal regions; tagging left and right determination labels based on the spinal baseline in each of the training images; generating each training image tagged with the left and right determination labels as training data; and training a pneumothorax prediction model by using the training data. Training the pneumothorax prediction model may comprise training the pneumothorax prediction model for each of a task of predicting pneumothorax, a task of predicting tubes, and a task of predicting the spinal baseline, with respect to at least one training image corresponding to the training data.

The generating the spinal baseline may comprise separating a spinal region from each training image in which spinal region information is annotated, or separating a spinal region from each training image through a machine learning model learning a spinal region detection task.

The generating the spinal baseline may comprises post-processing pixels segmented into the spinal regions with a polynomial regression algorithm to generate a baseline.

The pneumothorax detection method may further comprise inputting a requested image into the trained pneumothorax prediction model; obtaining predicted pneumothorax information, predicted tube information, and a predicted spinal baseline with respect to the requested image from the pneumothorax prediction model; separating a prediction image in which the predicted pneumothorax information and the predicted tube information are displayed into two regions by using the predicted spinal baseline; and determining whether the requested image indicates an emergency by comparing regions in which the predicted pneumothorax information and the predicted tube information exist among the two regions.

The determining whether the request image indicates the emergency may comprise classifying the request image as an emergency pneumothorax when the predicted tube information does not exist in a region in which the predicted pneumothorax information exists, and classifying the request image as a general pneumothorax when the predicted tube information exists in the region in which the predicted pneumothorax information exists.

Some embodiments of the present disclosure provide a computing device. The computing device may comprise a memory; and at least one processor that executes instructions of a program loaded in the memory. The program may comprise instructions for inputting a requested image to a pneumothorax prediction model; obtaining predicted pneumothorax information, predicted tube information, and a predicted spinal baseline with respect to the requested image from the pneumothorax prediction model; separating a prediction image in which the predicted pneumothorax information and the predicted tube information are displayed into two regions, by using the predicted spinal baseline; and determining whether the requested image indicates an emergency by comparing regions in which the predicted pneumothorax information and the predicted tube information exist among the two regions.

The program may comprise the pneumothorax prediction model trained for a task of predicting pneumothorax in an input image, a task of predicting a tube in the input image, and a task of predicting the spinal baseline in the input image.

The determining whether the request image indicates an emergency may comprise determining whether the request image indicates an emergency comprises: determining at least one pneumothorax representative position for the predicted pneumothorax information and at least one tube representative position for the predicted tube information in the prediction image; determining a region in which the at least one pneumothorax representative position and the at least one tube representative position exist among two regions of the prediction image segmented by using the predicted spinal baseline; and classifying the requested image as an emergency pneumothorax when the tube representative position does not exist in a region in which the at least one pneumothorax representative position exists.

According to the embodiments, it is possible to predict pneumothorax from an image through a pneumothorax prediction model, and to predict whether a treated tube is present or not and a spinal baseline of a patient being a reference for determining left and right regions. Thus, an emergency pneumothorax required an emergency procedure is quickly and accurately determined.

According to the embodiments, since left and right regions of each patient can be determined without error by using a spinal baseline of a patient predicted from an image, it is possible to predict pneumothorax without being affected by the patient's photographing posture and physical characteristics.

DETAILED DESCRIPTION OF THE EMBODIMENTS

Figure 1:
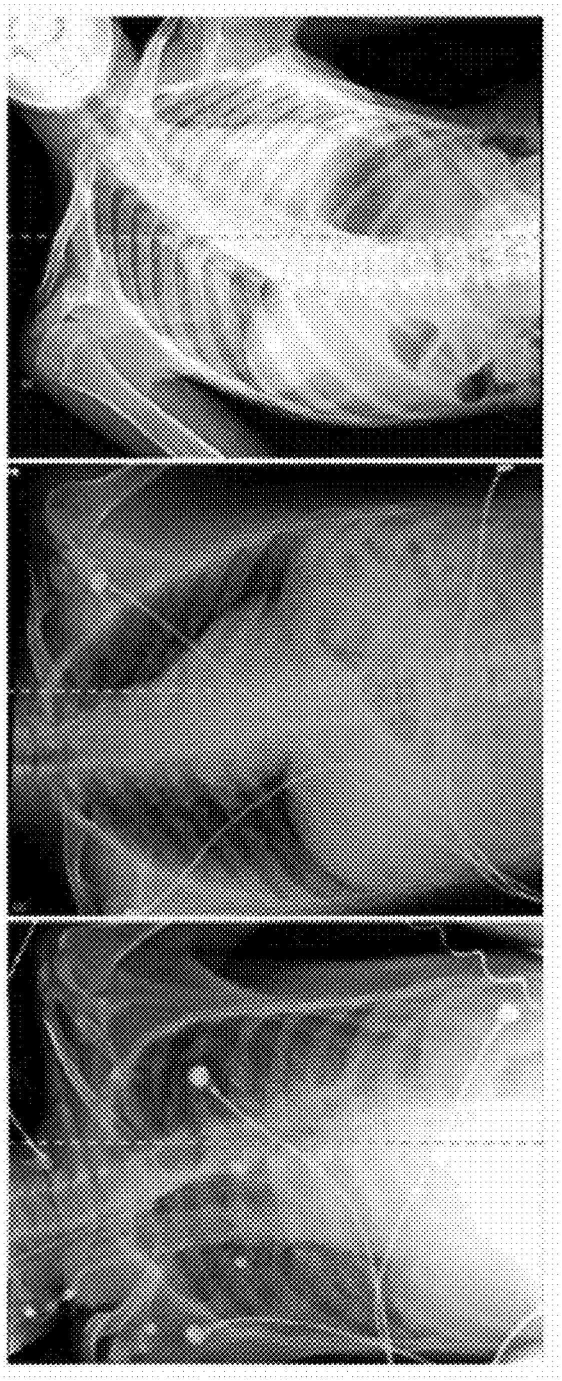
FIG. 1 exemplarily illustrates left and right asymmetric patient images.

Hereinafter, the present disclosure will be described more fully with reference to the accompanying drawings, in which exemplary embodiments of the invention are shown. As those skilled in the art would realize, the described embodiments may be modified in various different ways, all without departing from the spirit or scope of the present disclosure. Accordingly, the drawings and description are to be regarded as illustrative in nature and not restrictive, and like reference numerals designate like elements throughout the specification.

In the specification, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function or operation, and can be implemented by hardware components or software components and combinations thereof.

In the specification, the term "task" refers to as a task solved through machine learning or a task performed through machine learning. For example, when recognition, classification, prediction, etc. are performed on an anomaly from a medical image, each of the anomaly recognition, the anomaly classification, and the anomaly prediction may correspond to an individual task. The pneumothorax detection model of the present disclosure may be a machine learning model for learning at least one task, which may be implemented with software executed by a computing device. A program including instructions written to execute an operation of the present disclosure may be downloaded over a network or sold in a product form.

According to the present disclosure, left and right regions finally provided to medical staff are preferably provided as left and right regions of a patient divided based on the spine of the patient. In this case, a computing device may map a left side of an image to a right side of the patient, map a right side of the image to the left side of the patient, and then determine whether pneumothorax or the like is present in patient-reference left or right sides. In addition, the computing device may be implemented to determine whether the pneumothorax or the like is present in an image-reference left or right region in an intermediate stage, and then change the left and right according to the patient in an output stage. Alternatively, the computing device may be implemented to determine whether the pneumothorax or the like is present in a first or second region of the image without distinguishing left and right directions in the intermediate stage, and then change the left and right regions according to the patient in the output stage.

FIG. 1 exemplarily illustrates left and right asymmetric images.

Referring to FIG. 1, pneumothorax is a disease in which the lungs are pressed to be unable to normally breathe when air is filled in a pleural cavity surrounding the lungs. Medical staff should perform a treatment of quickly inserting a tube into the pleural cavity where the pneumothorax is formed, for discharging air. Since a patient with pneumothorax needs an emergency treatment, when an image analysis system can accurately and quickly predict pneumothorax from an image, it is possible to reduce damage of the emergency patient.

However, until now, most image analysis systems predict an abnormal symptom from a whole image. Even if the pneumothorax can be predicted and the predicted pneumothorax position can be displayed on the image, it is difficult to determine whether the predicted pneumothorax is in the patient's left region (the region where the left lung is present) or in the patient's right region (the region where the right lung is present). When an image is always taken in a standard posture required during photographing, the image analysis system may be designed to determine a region where the pneumothorax is found by dividing left and right regions with respect to a center of the image. However, this simple dividing method may make a mistake about a patient being difficult to maintain the standard posture in particular situation due to shortness of breath and chest pain, or about a patient being difficult to maintain the standard posture by a physical characteristics. For example, when an image in which the posture of the patient is not symmetrically photographed is inputted, as shown in FIG. 1, there is a big problem that the left and right regions where the pneumothorax is located may be incorrectly determined.

Meanwhile, medical staff may find pneumothorax on an X-ray image, and at the same time, determine whether the pneumothorax is located in the left lung or right lung of the patient. Therefore, even if the medical staff sees an image in which the posture of the patient is not symmetrically photographed, as shown in FIG. 1, the medical staff may immediately know where to insert a tube.

Next, similarly to the medical staff's pneumothorax determining mechanism, a pneumothorax detection method for predicting pneumothorax from an image in consideration of the patient's photographing posture and physical characteristics, and determining a region where the pneumothorax is positioned in the patient's left and right regions, will be described. Furthermore, a method for detecting emergency pneumothorax by simultaneously predicting a treated tube will be described.

Figure 2:
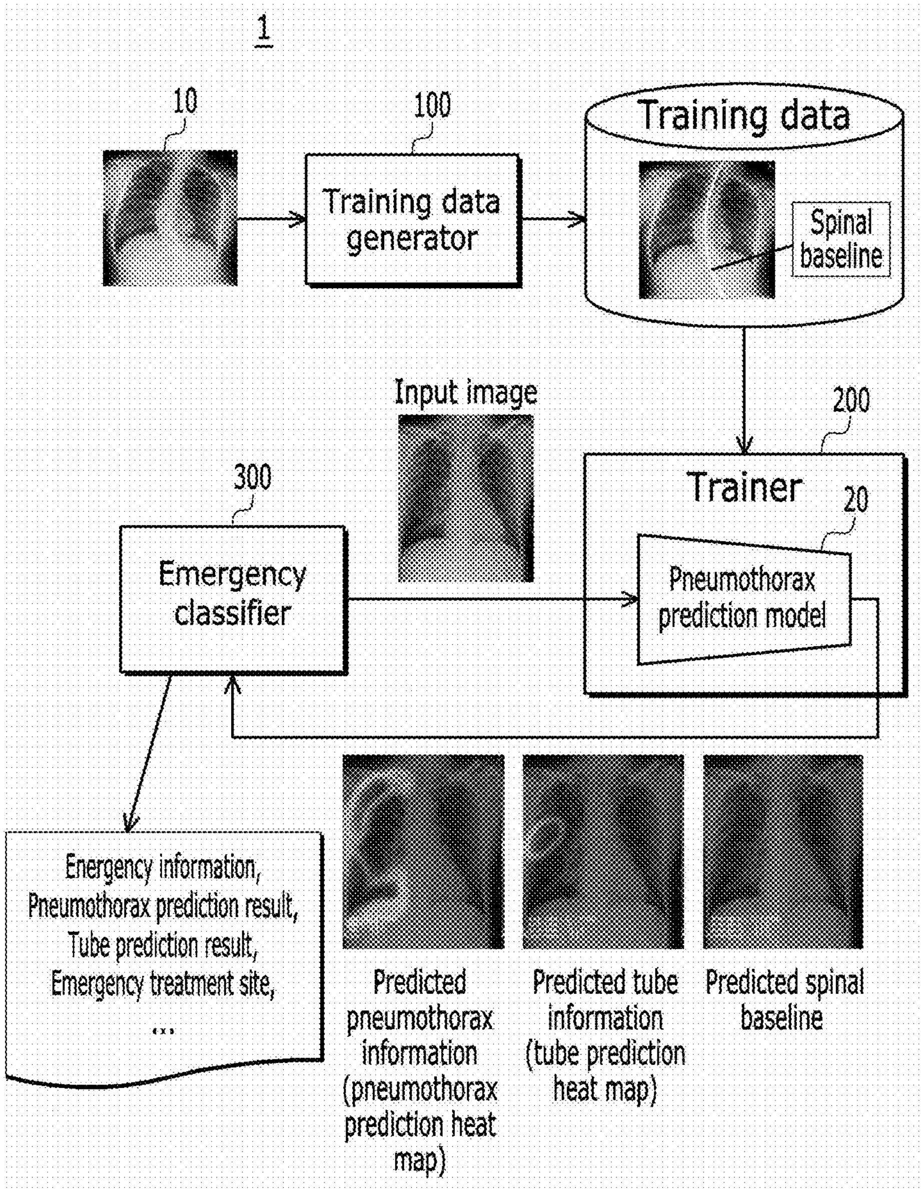
FIG. 2 and FIG. 3 respectively illustrate structural diagrams of a pneumothorax detection system according to an embodiment.
Figure 3:
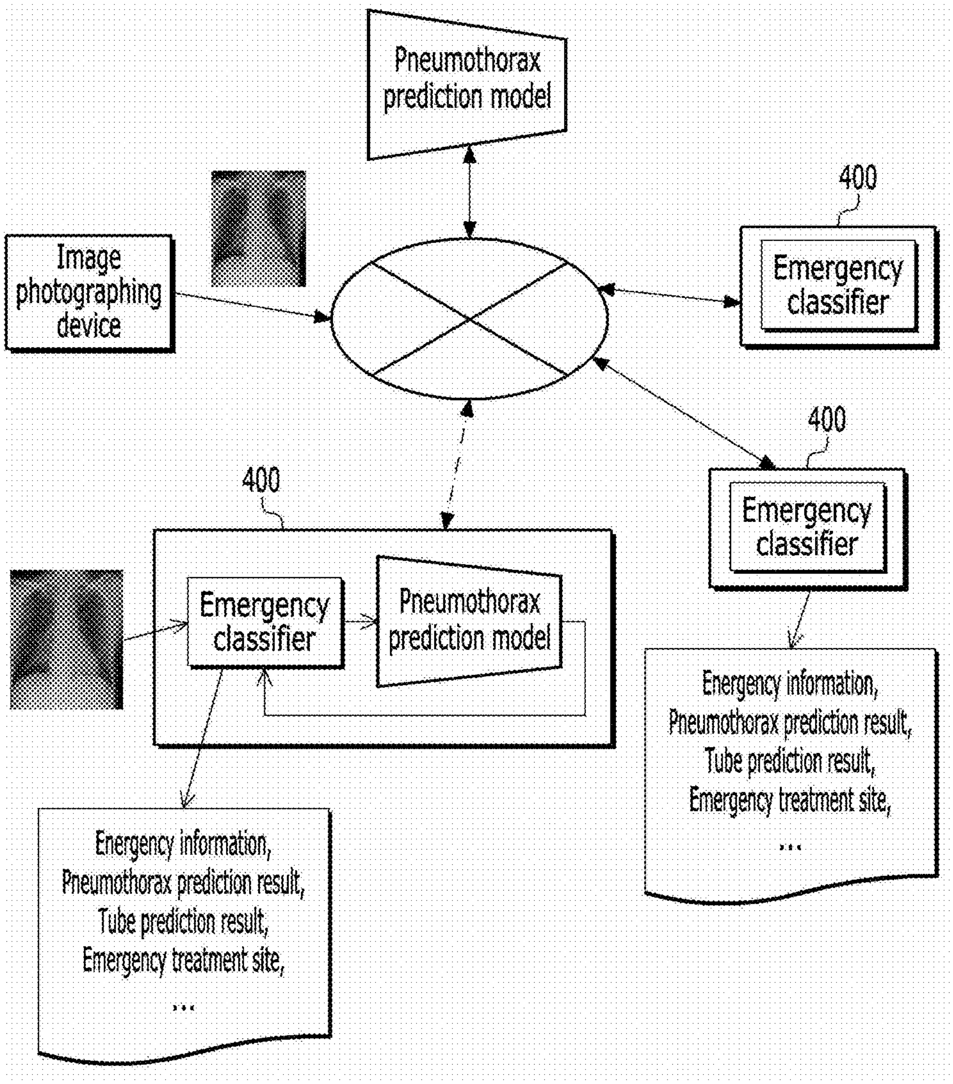
Figure 4:
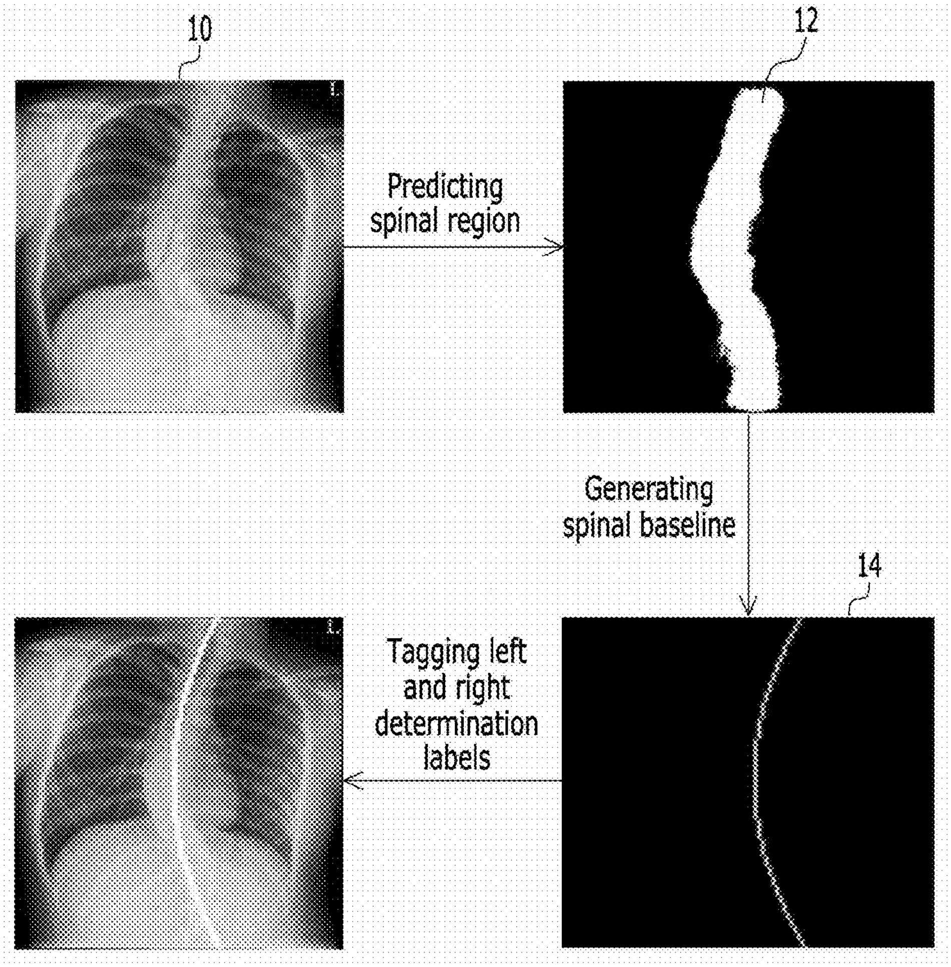
FIG. 4 illustrates a diagram for explaining a method of generating a learning image tagged with left and right determination labels according to an embodiment.
Figure 5:
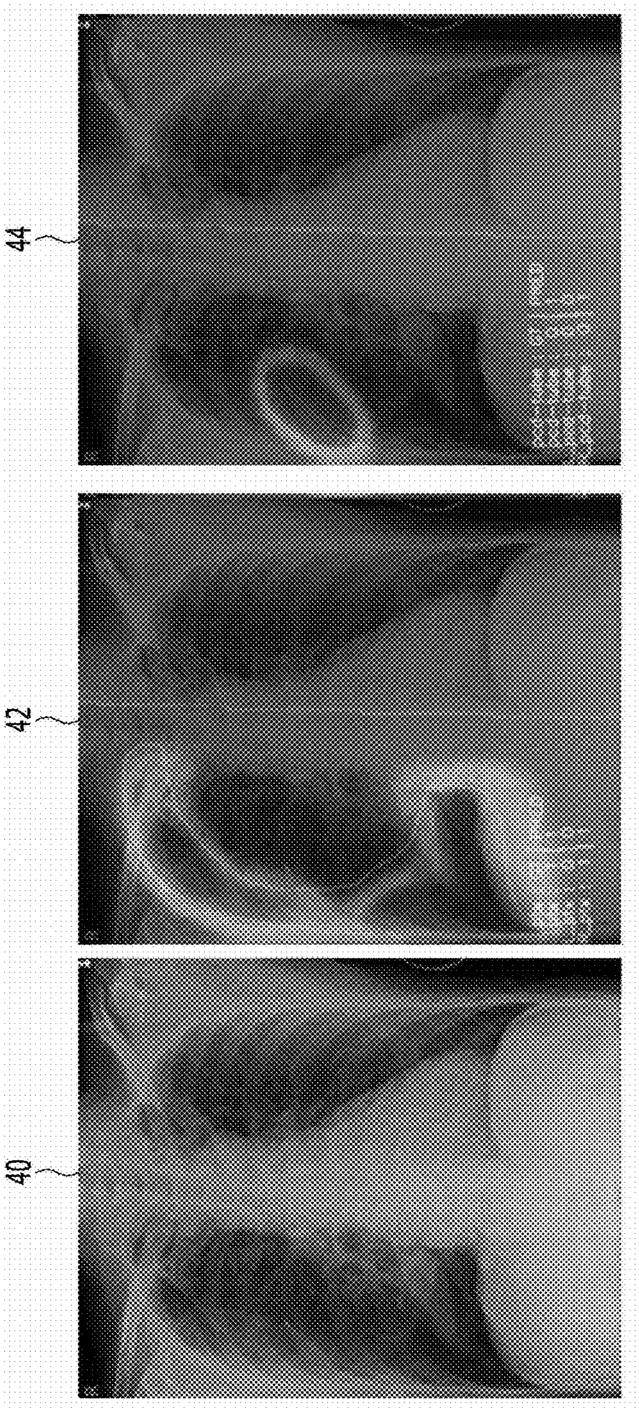
FIG. 5 illustrates a diagram for exemplarily explaining an emergency pneumothorax classifying method according to an embodiment.

FIG. 2 and FIG. 3 respectively illustrate structural diagrams of a pneumothorax detection system according to an embodiment, FIG. 4 illustrates a diagram for explaining a method of generating a training image tagged with left and right determination labels according to an embodiment, and FIG. 5 illustrates a diagram for exemplarily explaining an emergency pneumothorax classifying method according to an embodiment.

Referring to FIG. 2, a pneumothorax detection system 1 may include a training data generator 100 for generating training data from images 10, a trainer 200 for training a pneumothorax prediction model 20, and an emergency classifier 300 for classifying pneumothorax emergency patients by using the trained pneumothorax prediction model 20. For purposes of explanation, the above-mentioned elements are referred to as the training data generator 100, the trainer 200, and the emergency classifier 300. The training data generator 100, the trainer 200, and the emergency classifier 300 may be a computing device operated by at least one processor. Here, the training data generator 100, the trainer 200, and the emergency classifier 300 may be implemented with one computing device or distributed in separate computing devices. When distributed in the separate computing devices, the training data generator 100, the trainer 200, and the emergency classifier 300 may communicate with each other through a communication interface. The computing device may be any device capable of executing a software program having instructions written to perform the present disclosure. The computing device may be, for example, a server, a laptop computer, or the like.

Each of the training data generator 100, the trainer 200, and the emergency classifier 300 may be or have one artificial intelligence model or may be implemented with a plurality of artificial intelligence models. The pneumothorax prediction model 20 may also be one artificial intelligence model or may be implemented with a plurality of artificial intelligence models. The pneumothorax detection system 1 may be one artificial intelligence model or may be implemented with a plurality of artificial intelligence models. Accordingly, one or more artificial intelligence models corresponding to the above-described constituent elements may be implemented by one or more computing devices.

Referring to FIG. 3, a pneumothorax prediction model in which learning is completed in the trainer 200 and the software implemented in the emergency classifier 300 may operate in one computing device 400. There may be multiple computing devices 400, and the multiple computing devices 400 may operate individually, for example, at various sites (e.g., hospitals, different locations within one or more hospitals). Alternatively, the pneumothorax prediction model in which the learning is completed in the trainer 200 may be located at a server, and the computing devices 400 having the emergency classifier 300 may access the server through a network.

In addition, functions described in the present disclosure may be variously separated or integrated according to a service type. For example, client devices at various sites (e.g., hospitals, different locations in one or more hospitals) may request image analysis from the server via the network. An image captured by an image photographing device may be requested from the server through the network. Then, the server may transmit a report on a pneumothorax prediction result, Emergency information, an emergency treatment site (for example, a left region of a patient), and the like with respect to the requested image to the client device.

Referring back to FIG. 2, the training data generator 100 receives the images 10 used to train the pneumothorax prediction model. The training data generator 100 predicts a spine region in each image, and generates a spinal baseline that is a reference for determining left and right regions of the patient. The training data generator 100 generates the left and right determined labels that are generated based on the spinal baseline as training data of a pneumothorax prediction model. The image may be a chest x-ray image, but may be an image photographed by another type of device according to a medical technology. The training data may be generated according to a type and structure of the pneumothorax prediction model and a learning method. For example, at least some of the images may include data of pneumothorax information and/or tube information that is tagged with a label, or may be unlabeled data.

Since there are not many images annotated with spine information, it is difficult of the pneumothorax prediction model to learn a task to determine left and right from the images. Therefore, the training data generator 100 may learn a task of predicting a spinal region of an image in which the spinal region is not annotated, by using the training images annotated with the spinal region. The learned training data generator 100 may predict a spinal region in the images 10 used for training the pneumothorax prediction model, and generate a spinal baseline that is a reference for determining left and right regions of a patient in each image.

Meanwhile, when some of the images 10 used for training the pneumothorax prediction model are annotated with spinal region information, the training data generator 100 may separate the annotated spinal region from the corresponding image and generate a spinal baseline.

Referring to FIG. 4, the training data generator 100 receives the image 10. When the spinal region is not annotated in the image 10, the training data generator 100 that has learned to predict the spinal region predicts the spinal region in the image 10 and segments a predicted spinal region 12. The training data generator 100 post-processes pixels segmented into the spinal region 12 to generate a spinal baseline 14 representing the spinal region. The training data generator 100 may post-process the pixels segmented into the spinal region 12 by an algorithm such as polynomial regression to generate the spinal baseline 14.

The training data generator 100 may generate left and right determination labels based on the spinal baseline 14. The training data generator 100 may divide the left and right regions based on the spinal baseline 14 and generate labels for the divided left and right regions. Since the left and right determination labels do not need to be accurate in right and left, pseudo-labels may be tagged (annotated) in the left region and the right region. The left and right regions may be divided based on, for example, the location of the heart. That is, in the two regions divided by the spinal baseline 14, the region where the heart is present may be tagged with the label of the left region of the patient, and the region where the heart is not present may be tagged with the label of the right region of the patient. Alternatively, the two regions may be tagged with the left and right determination labels without distinguishing the right and left regions as a first region and a second region which are divided into the spinal baseline.

As such, the left and right determination labels, which are image labels divided into the left region and the right region based on the spinal baseline 14, are inputted to the pneumothorax prediction model together with the image 10. The left and right determination labels are used as data to learn the pneumothorax prediction model to predict the left and right regions simultaneously with pneumothorax prediction.

The training data generator 100 generates an image tagged with the left and right determination labels as training data. The training data is stored in a specified storage. The left and right determination labels described above may or may not coincide with actual left side and right side of the patient. As will be described later, the present disclosure is for providing information on whether the pneumothorax is an emergency, by determining whether a region in which pneumothorax has been found, and a region in which an emergency treatment (e.g., a tube insertion treatment) is needed, are the same region. Therefore the right and left of the actual patient and the left and right determination labels tagged to determine the emergency pneumothorax may not be the same.

There may be various methods for separating the spine region 12 from the image 10.

According to an embodiment, when information on the spine region is annotated in the image 10, the training data generator 100 may separate the annotated spine region 12 from the image 10.

According to another embodiment, the training data generator 100 may predict and separate the spine region 12 from the image 10 through machine learning-based segmentation.

The training data generator 100 may train a machine learning model for a task of detecting a spine region in an image. The machine learning model may be, for example, a convolutional neural network model. The training data generator 100 may train a machine learning model with a medical image and data annotated with information on a spinal region included in the corresponding medical image, and predict and separate the spinal region 12 of the inputted image 10 through the learned machine learning model. In addition, the training data generator 100 may find a center line representing the spine region from pixels of the spinal region by using a polynomial regression algorithm, and determine the center line as the spinal baseline 14.

According to yet another embodiment, the training data generator 100 may train the machine learning model for a task of finding a center line that best follows the annotated spine region. The training data generator 100 may find the center line that best follows the spine region 12 of the input image 10 through the learned machine learning model, and determine the center line as the spinal baseline 14.

The spinal baseline 14 may be generated by applying the polynomial regression algorithm to the pixels of the segmented spinal region. In this case, the training data generator 100 may divide the spine region into a plurality of regions, and then connect center lines extracted for respective regions to generate the spinal baseline. Alternatively, the training data generator 100 may divide the spine region into a plurality of regions, find center points of respective regions, and generate a spinal baseline by connecting the center points of the regions.

Referring back to FIG. 2, the trainer 200 may receive the images tagged (annotated) with the left and right determination labels as the training data, and train the pneumothorax prediction model 20 by using the training data. The pneumothorax prediction model 20 learns a task of predicting pneumothorax in the input image and a task of predicting the spinal baseline for discriminating the left and right regions of the patient from the input image. In this case, the pneumothorax prediction model 20 may simultaneously learn a task of predicting the tube from the input image. The task of predicting pneumothorax in the input image may be a task of outputting a value at which the pixels of the image are predicted as pneumothorax. The task of predicting the tube in the input image may be a task of outputting a value at which the pixels of the image are predicted as a tube. The task of determining the left and right regions of the patient in the input image may be a task of outputting a value at which the pixels of the image are predicted with the spinal baseline, or a task of predicting the left and right regions (or the first and second regions) based on the predicted spinal baseline. In the description, the prediction of the spinal baseline is described.

The pneumothorax prediction model may be trained based on the annotated image for each of the pneumothorax, the spine, and the tube. In this case, without the help of the trainer 200 described above, the pneumothorax prediction model may be trained. The pneumothorax prediction model may learn respective tasks for the pneumothorax, the spine, and the tube at once.

The pneumothorax prediction model 20 may output pneumothorax information, tube information, and the predicted spinal baseline that are predicted from the input image. The pneumothorax information and the tube information may include prediction values calculated for each pixel. The pneumothorax and tube prediction values may be visually displayed on the input image. For example, a heat map according to the prediction value may be displayed as a prediction image in which the prediction value is displayed. The emergency classifier 300 classifies pneumothorax patients based on the pneumothorax information, the tube information, and the spinal baseline outputted from the trained pneumothorax prediction model 20. The emergency classifier 300 may classify the pneumothorax into, for example, an emergency pneumothorax requiring an emergency treatment and a general pneumothorax not requiring the emergency treatment. The emergency treatment for the emergency pneumothorax may include a tube insertion treatment. The emergency classifier 300 may also classify cases that are not expected to be pneumothorax. For example, the emergency classifier 300 may classify normal or other lesions without the pneumothorax.

When classifying pneumothorax patients, a pneumothorax patient treated the tube insertion is not classified as an emergency patient. Therefore the emergency classifier 300 may not classify the patient as the emergency patient when the pneumothorax and the tube exist in the same region among the segmented regions based on the spinal baseline. While it may classify the patient as the emergency patient when there is no tube in the region where the pneumothorax is found. The emergency classifier 300 may first find the region in which the pneumothorax is predicted, and classify the input image as an emergency when there is no tube in the region in which the pneumothorax is predicted. The emergency classifier 300 may classify the input image as an emergency when there is no tube in the region in which the pneumothorax is predicted, and output patient region information (e.g., the left lung region of the patient) requiring a tube insertion treatment along with information with respect to the emergency pneumothorax.

Referring to FIG. 5, the emergency classifier 300 may determine the left and right regions based on a spinal baseline prediction value outputted from the pneumothorax prediction model 20 with respect to an input image 40. The spinal baseline prediction value may mean a prediction value for the above-described spinal baseline. The emergency classifier 300 may determine a region including a pneumothorax prediction heat map in a pneumothorax prediction image 42. For example, the emergency classifier 300 may determine a region including the prediction heat map among left and right regions (or first and second regions) of the pneumothorax prediction image 42, and determine a region in which the pneumothorax is present based on the pneumothorax prediction value. Specifically, the emergency classifier 300 may determine the region in which the pneumothorax is present based on the pneumothorax prediction value in the left region and the right region, which are divided based on the spinal baseline. Similarly, the emergency classifier 300 may determine a region in which the tube prediction heat map is located based on the spinal baseline prediction value. For example, the emergency classifier 300 may determine whether the region in which the tube prediction heat map is located is either of the left and right regions (or the first and second regions) in a tube prediction image 44, based on the spinal baseline, and may determine the region in which the tube is present based on the tube prediction value. The emergency classifier 300 may classify the input image as a general pneumothorax when the pneumothorax and the tube exist in the same region among the left and right regions segmented by the spinal baseline.

For example, when the pneumothorax in the right region with respect to a patient is predicted (R_ptx=1, L_ptx=0) and the tube in the right region with respect to the patient is predicted (R_tube=1, L_tube=0), the emergency classifier 300 may classify both the right and left regions as general rather than emergency (R_emergency=0, L_emergency=0).

When the pneumothorax in the right region with respect to the patient is predicted (R_ptx=1, L_ptx=0), and the tube in the left region with respect to the patient is predicted (R_tube=0, L_tube=1) or the tube is not predicted (R_tube=0, L_tube=0), the emergency classifier 300 may classify the right region with respect to the patient as emergency (R_emergency=1, L_emergency=0).

There may be various methods of determining, by the emergency classifier 300, whether the pneumothorax and the tube exist in the same region based on the pneumothorax prediction value, the tube prediction value, and the predicted spinal baseline.

According to an embodiment, the emergency classifier 300 may extract a maximum value of the pneumothorax prediction value and a maximum value of the tube prediction value from the prediction heat maps in which the pneumothorax prediction value and the tube prediction value with respect to the input image are displayed, respectively. The emergency classifier 300 may identify regions including positions of the maximum value of the pneumothorax prediction value and the maximum value of the tube prediction value among the two regions (the first region and the second region) that are divided based on the predicted spinal baseline. The emergency classifier 300 may determine whether the pneumothorax and the tube are present in the same region based on the positions of the maximum values. When the maximum value of the pneumothorax prediction value and the maximum value of the tube prediction value exceed a positive determination threshold, they may be determined as 'POSITIVE'.

According to another embodiment, the emergency classifier 300 may draw a contour connecting points at which the pneumothorax prediction value is greater than or equal to the threshold and a contour connecting points at which the tube prediction value is greater than or equal to the threshold value, in the prediction images including respective prediction heat maps for the pneumothorax and the tube. Then, it may confirm the region including the position of the maximum value of each region and determine whether the pneumothorax and the tube exist in the same region based on the position of the maximum value. When the maximum value of each region exceeds the positive determination threshold, it may be determined as 'POSITIVE'.

According to yet another embodiment, the emergency classifier 300 may draw a contour connecting points at which the pneumothorax prediction value is greater than or equal to the threshold and a contour connecting points at which the tube prediction value is greater than or equal to the threshold value, in the predictive images including respective prediction heat maps for the pneumothorax and the tube. Then, it may confirm a region including a position of a central value of each region and determine whether the pneumothorax and the tube exist in the same region based on the position of the central value. When the maximum value of each region exceeds the positive determination threshold, it may be determined as 'POSITIVE'.

According to another embodiment, the emergency classifier 300 may draw a contour connecting points at which the pneumothorax prediction value is greater than or equal to the threshold and a contour connecting points at which the tube prediction value is greater than or equal to the threshold value, in the predictive images including respective prediction heat maps for the pneumothorax and the tube. Then, it may confirm a region in which pixels included in each region are distributed more and determine as 'POSITIVE' when a maximum value of the region in which the pixels is distributed more exceeds the positive determination threshold.

Figure 6:
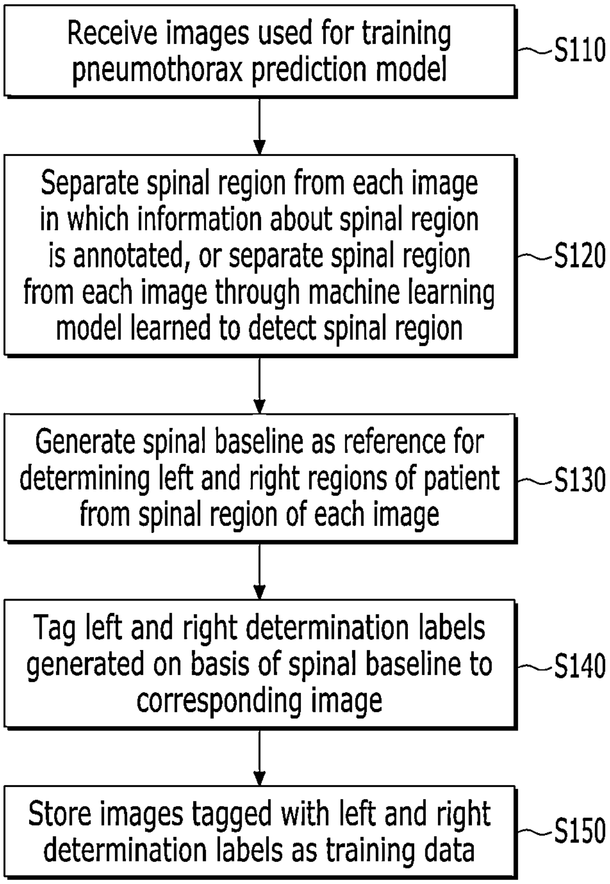
FIG. 6 illustrates a flowchart of a method of generating learning data of a pneumothorax detection model according to an embodiment.

FIG. 6 illustrates a flowchart of a method of generating training data of a pneumothorax detection model according to an embodiment.

Referring to FIG. 6, the training data generator 100 receives images used for training the pneumothorax prediction model in operation S110.

The training data generator 100 separates a spinal region from each image in which information about the spinal region is annotated, or separates the spinal region from each image through a machine learning model learned to detect the spinal region in operation S120.

The training data generator 100 generates a spinal baseline as a reference for determining the left and right regions of the patient from the spinal region of each image in operation S130. The pixels segmented into the spinal regions may be post-processed using a polynomial regression algorithm to generate the baseline.

The training data generator 100 tags the left and right determination labels generated on the basis of the spinal baseline to the corresponding image in operation S140. The left and right determination labels are labels for distinguishing the left region (or the first region) from the right region (or the second region), and may be pseudo-labels.

The training data generator 100 stores the images tagged with the left and right determination labels as training data in operation S150.

The images tagged with the left and right determination labels are used to train the pneumothorax prediction model 20. The trainer 200 receives the images tagged with the left and right determination labels, and trains the pneumothorax prediction model 20 with a task of predicting the pneumothorax in the input image (corresponding to the received image), a task of predicting the tube in the input image, and a task of predicting the spinal baseline for determining the left and right regions of the patient from the input image. The type, structure, and learning method of the pneumothorax prediction model 20 may be variously designed.

Figure 7:
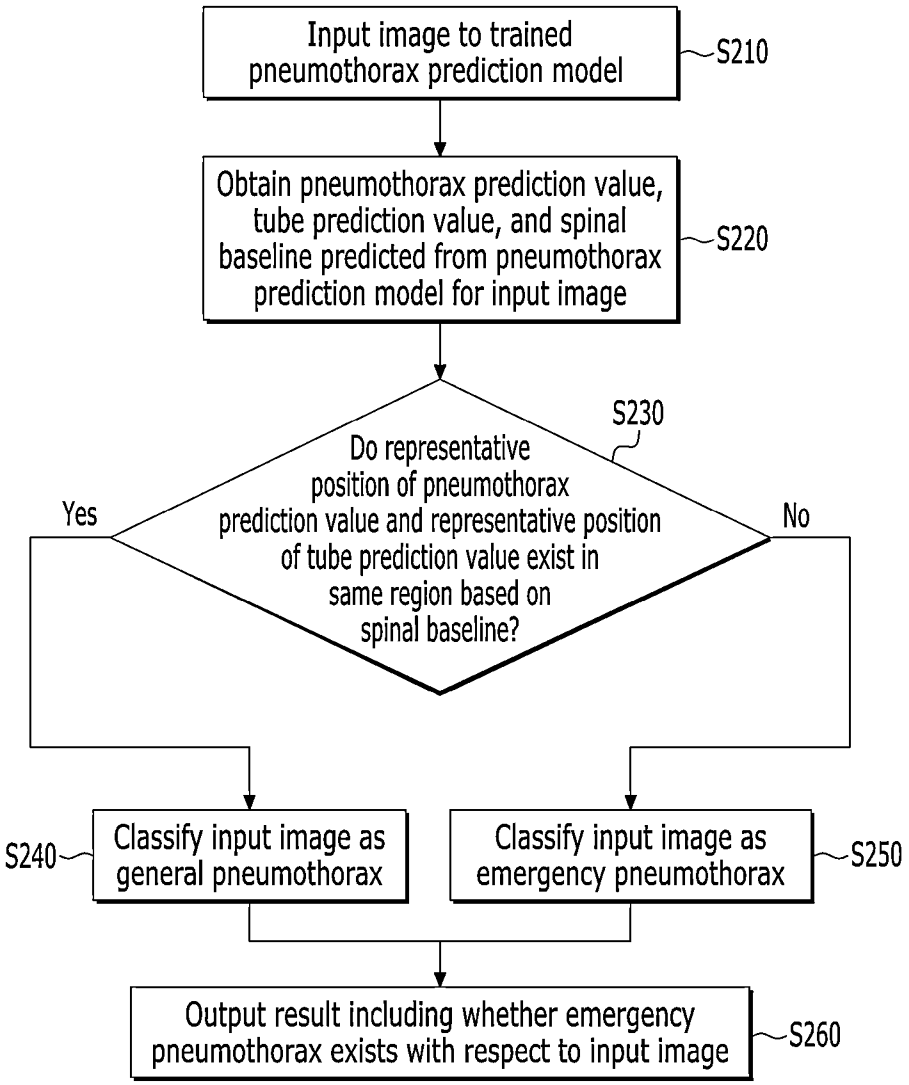
FIG. 7 illustrates a flowchart of a pneumothorax detection method using a pneumothorax detection model according to an embodiment.

FIG. 7 illustrates a flowchart of a pneumothorax detection method using a pneumothorax detection model according to an embodiment.

Referring to FIG. 7, the emergency classifier 300 inputs a request image to the trained pneumothorax prediction model 20 in operation S210.

The emergency classifier 300 obtains the predicted pneumothorax information (the pneumothorax prediction value), the predicted tube information (the tube prediction value), and the predicted spinal baseline from the pneumothorax prediction model 20 for the input image in operation S220. The pneumothorax information and the tube information may be respectively outputted to the prediction heat map in which the pneumothorax prediction value and the tube prediction value are displayed on the input image. An image including the prediction heat map may be called a predictive image.

The emergency classifier 300 determines whether the representative position of the pneumothorax information (the pneumothorax prediction value) and the representative position of the tube information (the tube prediction value) exist in the same region in the image divided into regions based on the spinal baseline in operation S230. The emergency classifier 300 may determine the pixel positions at which the pneumothorax prediction value and the tube prediction value are the maximum values as representative positions. The emergency classifier 300 may determine the regions based on the predictive values of the pneumothorax and the tube, and determine the pixel position of the maximum or central value in the region as the representative position of the pneumothorax prediction value or the tube prediction value.

When the representative position of the pneumothorax prediction value and the representative position of the tube prediction value exist in the same region, the emergency classifier 300 classifies the input image as the general pneumothorax in operation S240. That is, the emergency classifier 300 classifies the input image as the general pneumothorax because there is a treated tube in the region in which the pneumothorax is found.

The emergency classifier 300 classifies the input image as the emergency pneumothorax when the representative position of the tube prediction value does not exist in the region in which the representative position of the pneumothorax prediction value exists in operation S250. That is, the emergency classifier 300 classifies the input image as the emergency pneumothorax in which the emergency treatment, such as the tube insertion treatment, is required in the corresponding region (e.g., the left lung region of the patient) because no tube is found in the region where the pneumothorax is found.

The emergency classifier 300 outputs a result including whether or not the emergency pneumothorax exists with respect to the input image in operation S260. The emergency classifier 300 outputs a notification indicating the emergency pneumothorax in a case of the classified emergency. In this case, the emergency classifier 300 may output information on the emergency pneumothorax along with emergency information on whether or not the emergency pneumothorax exists in the input image. For example, the emergency classifier 300 may output various results such as a pneumothorax prediction result, a tube prediction result, and a site for an emergency tube insertion treatment (for example, a left lung region of a patient), as the information on the emergency pneumothorax.

As described above, the pneumothorax detection system 1 may predict a pneumothorax from an image through a pneumothorax prediction model, predict whether a treated tube is present or not and a spinal baseline of a patient, which is a basis for determining left and right regions, and thus may quickly and accurately determine whether an emergency pneumothorax to which an emergency treatment is required exists or not. Particularly, since left and right regions of each patient can be determined without error by using a spinal baseline of a patient predicted from an image, the pneumothorax detection system 1 may predict a pneumothorax without being affected by the patient's photographing posture, physical characteristics, and the like.

Figure 8:
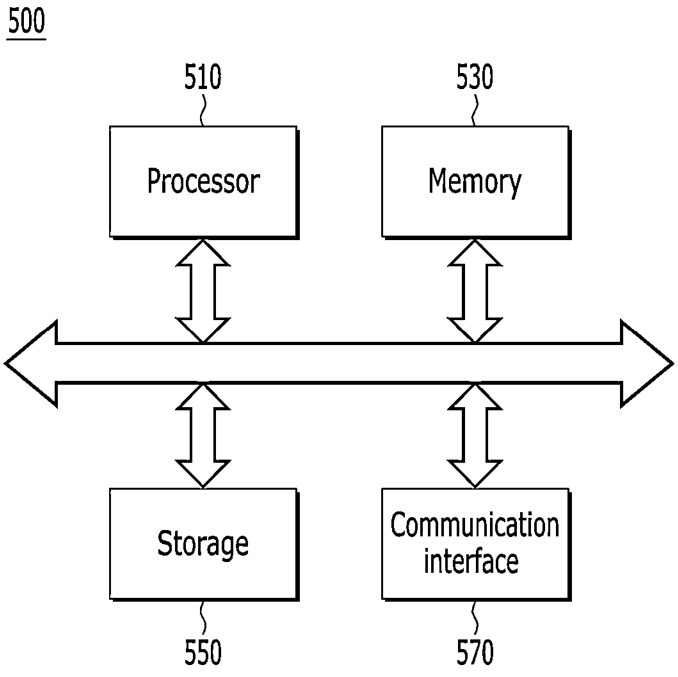
FIG. 8 illustrates a hardware configuration diagram of a computing device according to an embodiment.

FIG. 8 illustrates a hardware configuration diagram of a computing device according to an embodiment.

Referring to FIG. 8, the training data generator 100, the trainer 200, and the emergency classifier 300 may execute a program including instructions to perform operations of the present disclosure in a computing device 500 operated by at least one processor.

Hardware of the computing device 500 may include at least one processor 510, a memory 530, a storage 550, and a communication interface 570, which may be connected via a bus. In addition, hardware such as an input device and an output device may be included. The computing device 500 may be installed with an operating system capable of operating the program and various software.

The processor 510 controls the operation of the computing device 500, and it may be a processor of various types for processing instructions included in a program, for example, it may be a central processing unit (CPU), a microprocessor unit (MPU), a microcontroller unit (MCU), a graphics processing unit (GPU), or the like. The memory 530 loads a corresponding program such that the instructions for the operations of the present disclosure are executed by the processor 510. The memory 530 may be, for example, a read only memory (ROM), a random access memory (RAM), or the like. The storage 550 stores various data, programs, and the like required to perform the operations of the present disclosure. The communication interface 570 may be a wired/wireless communication module.

The above-described embodiments can be realized through a program for realizing functions corresponding to the configuration of the embodiments or a recording medium for recording the program in addition to through the above-described device and/or method, which is easily realized by a person skilled in the art.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An emergency patient classification method performed by a computing device, comprising:

receiving a medical image of a patient;

obtaining predicted pneumothorax information and predicted tube information from the medical image based on a trained pneumothorax prediction model;

obtaining a spinal baseline from the medical image based on the trained pneumothorax prediction model;

dividing the medical image into a left region and a right region based on the spinal baseline; and classifying a region among the left region and the right region as one of an emergency pneumothorax, a general pneumothorax, normal, or other lesions without the pneumothorax, based on the predicted pneumothorax information and the predicted tube information.

2. The emergency patient classification method of claim 1, wherein the classifying the region in the medical image comprises:

classifying the region in the medical image as the general pneumothorax, in response to determining that the region in which the pneumothorax exists includes a tube based on the predicted pneumothorax information and the predicted tube information.

3. The emergency patient classification method of claim 1, wherein the classifying the region in the medical image comprises:

classifying the region in the medical image as the emergency pneumothorax, in response to determining that the region in which the pneumothorax exists does not include a tube based on the predicted pneumothorax information and the predicted tube information.

4. The emergency patient classification method of claim 1, further comprising:

displaying information on whether the emergency pneumothorax exists in the medical image.

5. The emergency patient classification method of claim 1, wherein the classifying the region in the medical image comprises:

determining whether the pneumothorax and a tube exist in the same region among the left region and the right region.

6. The emergency patient classification method of claim 1, wherein the pneumothorax prediction model is trained to predict pneumothorax information and tube information by using training medical images tagged with left and right determination labels.

7. The emergency patient classification method of claim 1, further comprising:

displaying information related to the pneumothorax on the medical image; and wherein the information related to the pneumothorax includes at least one of the predicted pneumothorax information, the predicted tube information, or patient region information requiring a tube insertion treatment.

8. The emergency patient classification method of claim 7, wherein the displaying the information related to the pneumothorax comprises:

displaying the predicted pneumothorax information and/or the predicted tube information as a heat map.

9. The emergency patient classification method of claim 7, wherein displaying the information related to the pneumothorax comprises displaying the predicted pneumothorax information and/or the predicted tube information as a contour connecting points at which prediction value is greater than or equal to a threshold value.

10. A computing device comprising:

at least one memory; and at least one processor for executing instructions stored in the at least one memory, wherein the at least one processor is configured to:

receive a medical image of a patient;

obtain predicted pneumothorax information and predicted tube information from the medical image based on a trained pneumothorax prediction model;

obtain a spinal baseline from the medical image based on the trained pneumothorax prediction model;

divide the medical image into a left region and a right region based on the spinal baseline; and classify a region among the left region and the right region as one of an emergency pneumothorax, a general pneumothorax, normal, or other lesions without the pneumothorax, based on the predicted pneumothorax information and the predicted tube information.

11. The computing device of claim 10, wherein the at least one processor is configured to:

classify the region in the medical image as the general pneumothorax, in response to determining that the region in which the pneumothorax exists includes a tube based on the predicted pneumothorax information and the predicted tube information.

12. The computing device of claim 10, wherein the at least one processor is configured to:

classify the region in the medical image as the emergency pneumothorax, in response to determining that the region in which the pneumothorax exists does not include a tube based on the predicted pneumothorax information and the predicted tube information.

13. The computing device of claim 10, wherein the at least one processor is configured to:

display information on whether the emergency pneumothorax exists in the medical image.

14. The computing device of claim 10, wherein the at least one processor is configured to:

determine whether the pneumothorax and a tube exist in the same region among the left region and the right region.

15. The computing device of claim 10, wherein the pneumothorax prediction model is trained to predict pneumothorax information and tube information by using training medical images tagged with left and right determination labels.

16. The computing device of claim 10, wherein the at least one processor is configured to:

display information related to the pneumothorax on the medical image; and wherein the information related to the pneumothorax includes at least one of the predicted pneumothorax information, the predicted tube information, or patient region information requiring a tube insertion treatment.

17. The computing device of claim 16, wherein the at least one processor is configured to:

display the predicted pneumothorax information and/or the predicted tube information as a heat map.

18. The computing device of claim 16, wherein the at least one processor is configured to:

display the predicted pneumothorax information and/or the predicted tube information as a contour connecting points at which prediction value is greater than or equal to a threshold value.

* * * * *